(12) United States Patent
Montefusco

(10) Patent No.: US 7,726,211 B2
(45) Date of Patent: Jun. 1, 2010

(54) SCENT EVIDENCE COLLECTING AND TRANSFER DEVICE

(76) Inventor: Vincent Montefusco, P.O. Box 387, Mammoth Lakes, CA (US) 93546

(*) Notice: Subject to any disclaimer, the term of this patent is extended or adjusted under 35 U.S.C. 154(b) by 0 days.

(21) Appl. No.: 11/974,204

(22) Filed: Oct. 12, 2007

(65) Prior Publication Data

US 2009/0095093 A1    Apr. 16, 2009

(51) Int. Cl.
*G01N 1/24* (2006.01)
(52) U.S. Cl. .............. 73/863.71; 73/863.41; 73/863.81; 73/864.81
(58) Field of Classification Search ............ 73/863, 73/863.21, 863.22, 863.23, 863.71, 863.81, 73/864.81, 864.91, 864.71
See application file for complete search history.

(56) References Cited

U.S. PATENT DOCUMENTS

| | | | | |
|---|---|---|---|---|
| 2,458,508 A * | 1/1949 | Goetz | ...................... | 73/863.23 |
| 2,519,056 A * | 8/1950 | Lang | ........................ | 73/864.51 |
| 3,188,854 A * | 6/1965 | Hersch | .................... | 73/863.86 |
| 3,748,905 A * | 7/1973 | Fletcher et al. | .......... | 73/863.25 |
| 4,502,951 A * | 3/1985 | Koenig et al. | ................. | 209/21 |
| 4,675,034 A * | 6/1987 | Lynch et al. | ............. | 73/863.23 |
| 4,754,655 A * | 7/1988 | Parker et al. | ............. | 73/864.44 |
| 4,909,090 A * | 3/1990 | McGown et al. | ......... | 73/864.33 |
| 5,438,885 A * | 8/1995 | Zelazny | .................... | 73/864.71 |
| 5,827,982 A * | 10/1998 | Doutre et al. | ............ | 73/863.23 |
| 5,939,647 A * | 8/1999 | Chinn et al. | ............. | 73/864.71 |
| 6,427,543 B1 * | 8/2002 | Torrison | .................. | 73/863.33 |
| 7,122,065 B2 * | 10/2006 | Fox | .............................. | 55/306 |
| 7,257,990 B2 * | 8/2007 | Bujas et al. | .................... | 73/38 |
| 7,448,288 B2 * | 11/2008 | Montefusco | ............. | 73/864.34 |

* cited by examiner

*Primary Examiner*—David A. Rogers
(74) *Attorney, Agent, or Firm*—Irving Keschner

(57) ABSTRACT

An improved scent transfer device for collecting evidence at a crime scene. The device comprises a gas cartridge coupled to an air valve. A holder having a sterile pad positioned therein is secured to one end of a housing containing said air valve by locking protrusions. When gas from the cartridge is expelled into the air valve, a vacuum is created at the end of where the pad holder is attached when a switch is pressed, enabling a user to collect the scent on the pad. The pad can then be removed and stored in an evidence bag. An extension member which locks into the holder can be utilized to extend the capabilities of the device.

4 Claims, 2 Drawing Sheets

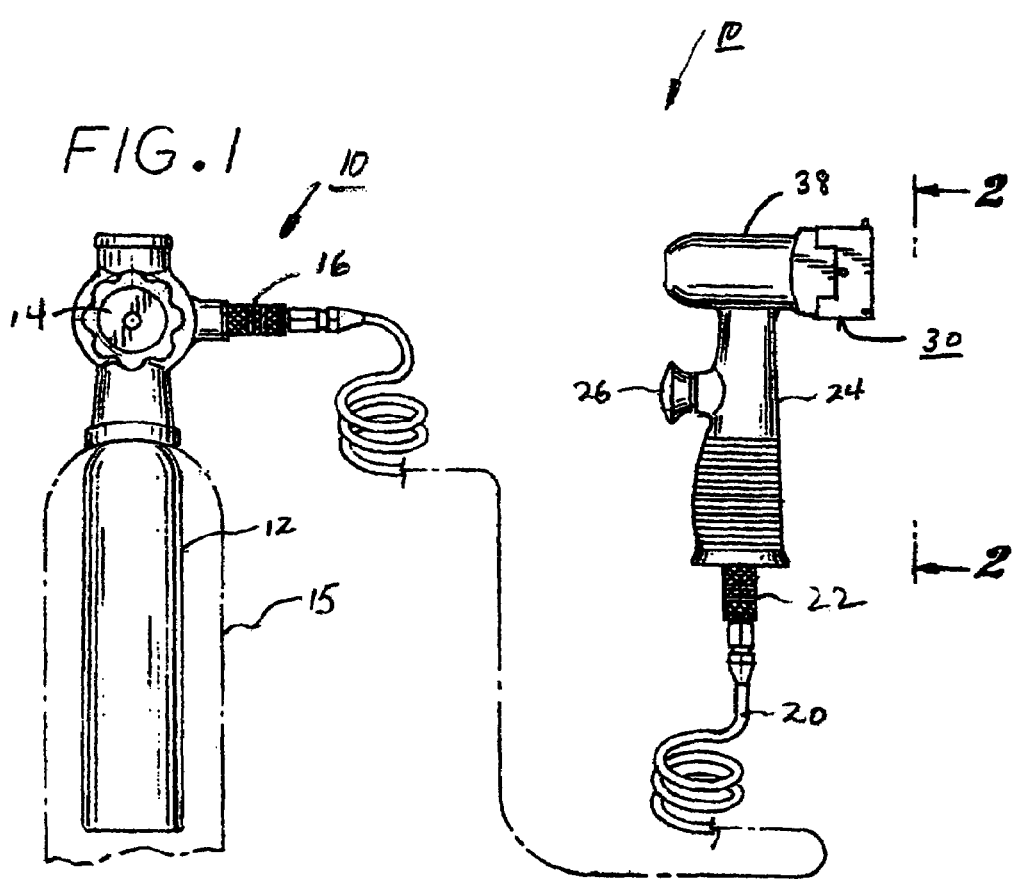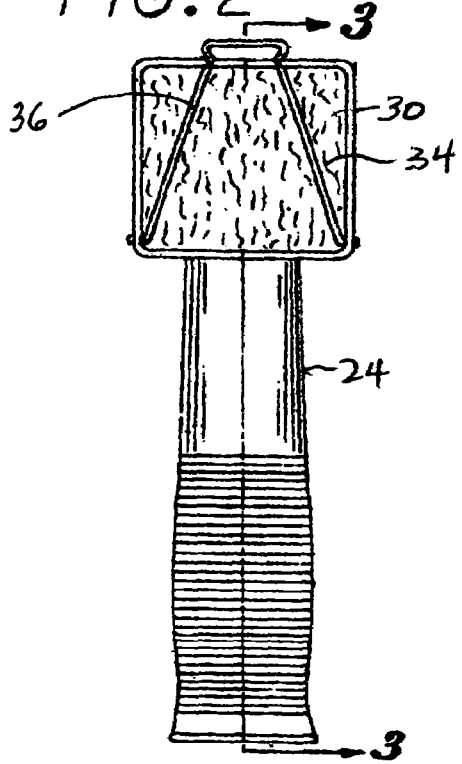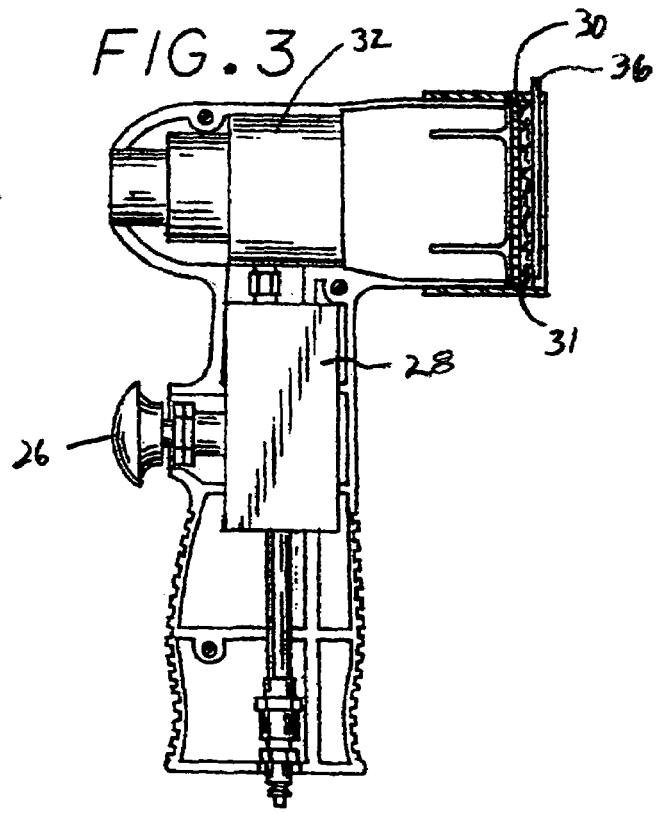

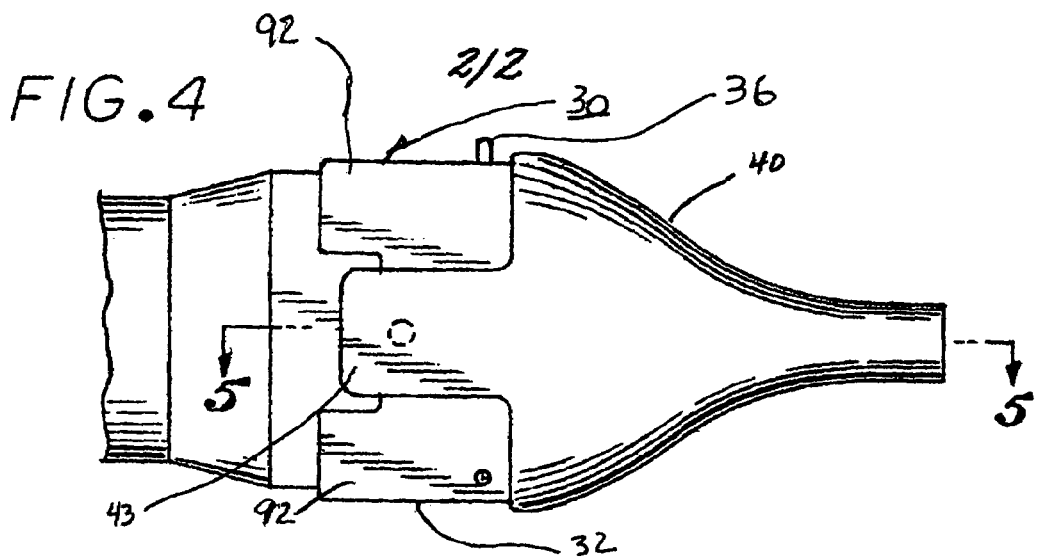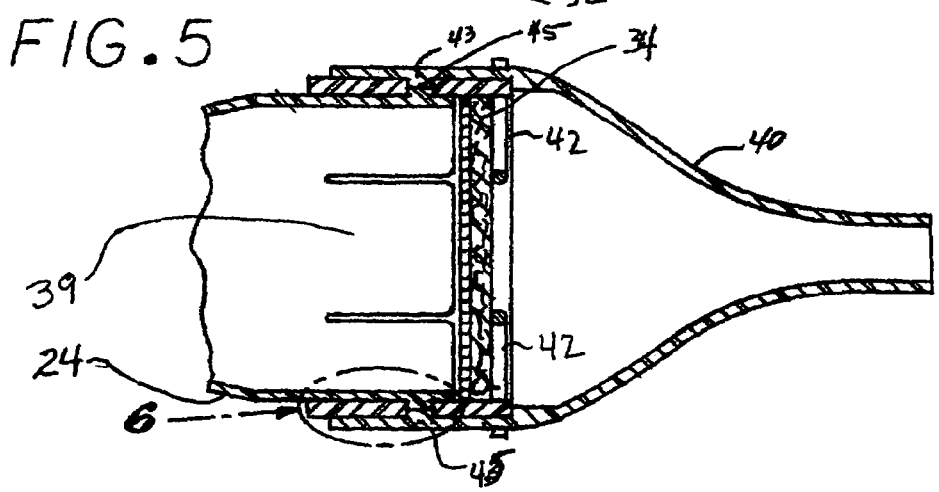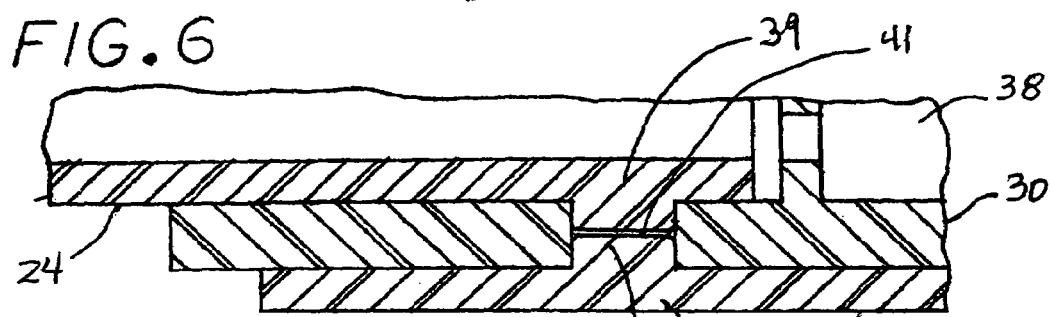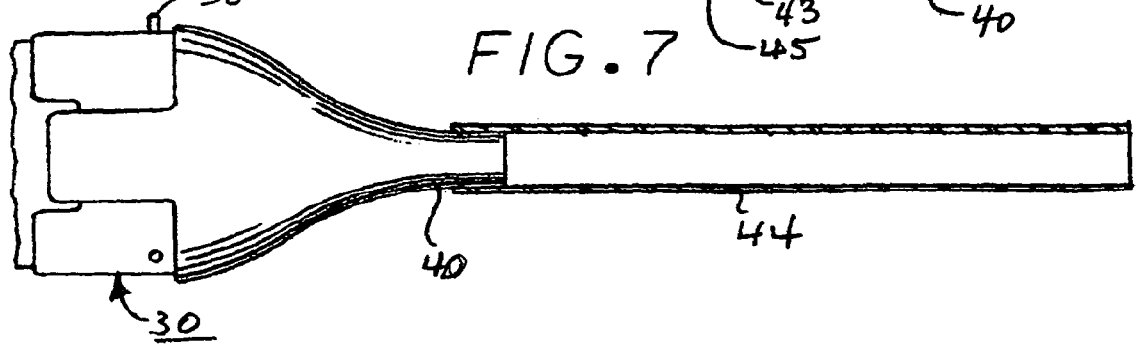

SCENT EVIDENCE COLLECTING AND TRANSFER DEVICE

BACKGROUND OF THE INVENTION

1. Field of the Invention

The present invention relates to a device for collecting scents from a scene and enabling trained dogs to sniff the collected scent and then hunt for criminals or missing persons.

2. Description of the Prior Art

Copending application Ser. No. 11/545,941, filed on Oct. 12, 2006, now Pat. No. 7,448,288, discloses an improved scent transfer device for collecting evidence at a crime scene. The device comprises an air inflator having a gas cartridge, the inflator being coupled to an air amplifier. A holder having a sterile pad positioned therein is secured to the air amplifier. When gas from the cartridge is expelled into the air amplifier, a vacuum is created at the end of the air amplifier where the pad holder is attached, enabling a user, when the pad holder is positioned near an area to be examined, to collect the scent on the pad. The pad can then be removed and stored in an evidence bag. The device of the present invention is light weight and does not require mechanical parts, such as a motor and batteries. In addition, the use of gas cartridges eliminates the necessity of using air to create the vacuum which could contaminate the pad and also enables the generated vacuum to be precisely metered each time the device is used.

What is desired is to provide a scent transfer device which is an improvement to the device shown in the '941 application wherein the pad holder is more secure to the device and an extension holder is provided, when necessary, to provide an extension mechanism whereby the scent holder device can be used in more varied environments. In addition, what is desired is to provide a housing that is ergonomic and which incorporates the basic components of the scent transfer unit.

SUMMARY OF THE INVENTION

The present invention provides a scent transfer device which has a housing designed to incorporate the basic components of the device and wherein the pad holder is modified such that it locks directly onto the housing and a nozzle tube extension holder locks onto the scent pad holder. These additional features provide a more rugged and versatile scent transfer device.

DESCRIPTION OF THE DRAWINGS

For a better understanding of the present invention as well as other objects and further features thereof, reference is made to the following description which is to be read in conjunction with the accompanying drawing therein:

FIG. 1 illustrates the scent transfer device of the present invention;

FIG. 2 is a view along line 2-2 of FIG. 1;

FIG. 3 is an internal view of a portion of the drive shown in FIG. 1;

FIG. 4 illustrates the pad holder utilized in the present invention;

FIG. 5 is a cross-sectional view along line 5-5 of FIG. 4;

FIG. 6 is a detail of the tab holder locking tabs shown in FIG. 5; and

FIG. 7 illustrates the nozzle tube extension holder locking onto the scent pad holder.

DESCRIPTION OF THE INVENTION

Referring now to the figures, the scent transfer device 10 of the present invention is illustrated. An inert gas bottle/cylinder 12 is coupled to gas regulator 14 and thence to quick connect fitting 16. The output from fitting 16 is coupled via a short inert gas air hose 20 to quick connect fitting 22 and thence to housing 24. An air control switch 26 is coupled to momentary air valve 28 as shown in FIG. 3. Housing 24 has an open end 38 with flexible tabs 39 and scent pad holder 30 has a rectangular shape (FIG. 2). Two opposing sides are formed with a tab 92 having a hole 41. The scent pad holder 30 is coupled to venturi device 32 that is located within the housing 24, and a scent pad 34 is positioned within the holder and held in place by a hold down clip 36. As shown in FIG. 4-6, the tabs 92 of the holder 30 fit over the tabs 39 at end 38 of the housing 24. The tabs 39 each has a small, round protrusion or button that snap into the respective holes 41 of the scent pad holder 30 thus securing the rod holder 30 to the main housing 24.

Nozzle adapter 40 enables a sized tube 44 to slip on the end of the scent pad holder 30. This enables scent to be collected from hard to reach places and holes that may be bored in walls, dirt, etc. Nozzle adapter 40 fits over scent pad holder 30 and has the same type of tab (clip) 43 and protrusion 45 features as on the end 38 of the main housing 24. The two holes 41 provided on the tabs 92 of the scent pad holder 30 also accept the buttons 45 on the tabs 43 of the nozzle adapter 40 and hold it in place. In order to remove the nozzle adapter 40, the user pulls slightly outward or on the tabs 43 and then pulls the nozzle adapter 40 from the scent pad holder 30. To remove scent pad holder 30 from the end 38 of the main housing 24, the tabs are pushed in slightly and the holder is then removed from the housing.

As noted above, the scent pad holder 30 has a small through hole 41 which is located on both sides of the holder. The tabs 39 on the end 38 are slightly pressed in and holder 30 is slipped onto the end 38. The tabs spring back and the tab buttons lock holder 30 in place. Note that the buttons on the tabs 39 are designed not to be flush with the side of the scent pad holder 30. Rather, the buttons on the tabs 39 are approximately one-half the depth of the holes 41 as illustrated in FIG. 6.

The optional nozzle tube holder 40 has two spring-like flexible tabs 43 with small protrusions, or buttons, 45 on the underside of the tabs. The tabs are slightly spread to enable it to fit over scent pad holder 30. The nozzle tube holder buttons mate with the holes of the scent pad holder locking the nozzle tube holder to the scent pad holder 30. In essence, the scent pad holder holes are the same hole for both the housing tab buttons and the nozzle tube holder buttons. The nozzle tube holder is now secured in place. To remove the nozzle tube holder, the two tabs are slightly spread releasing the buttons 43 from the scent pad holder 30. The scent pad holder 30 is removed from the main housing 30 by slightly pushing in on the main housing tabs, thus releasing the scent pad holder 30 from main housing 38.

An optional nozzle 40 can be coupled to the scent pad holder via prongs 42 and an extension tube 44 fitted over the end 46 of the nozzle 40 as shown. The length of the extension tube 44 is determined in the field.

Device 10 operates in a similar manner to the device disclosed in co-pending application '941 and the teachings necessary thereof for an understanding of the present invention are incorporated herein. In essence, a scent pad 34 is secured within the pad holder 30 by hold down clip 36 as described in the co-pending application. The pad holder 30 is then locked onto the end 50 of housing 24 as described hereinabove and the extension tube 44, if required, is attached to the end of the pad holder. The user then positions the device adjacent the area wherein the scent is to be collected and the user then pushes switch 26 causing a vacuum to be produced by device valve 28, causing scent to be formed on the pad 34. After collecting the scent, pad holder 30 is removed from device 10, clip 36 is opened and the pad 34 removed and placed in a collection box.

While the invention has been described with reference to its preferred embodiments, it will be understood by those skilled in the art that various changes may be made and equivalents may be substituted for elements thereof without departing from the true spirit and scope of the invention. In addition, many modifications may be made to adapt a particular situation or material to the teachings of the invention without departing from its essential teachings.

What is claimed is:

1. A device for collecting a scent comprising:
    a cartridge having a pressurized gas container therein;
    first means coupled to said gas cartridge, said first means having a member for controlling the expulsion of said pressurized gas and a attachment member;
    second means having first and second ends, said first end being coupled to said attachment member for receiving gas expelled from said gas cartridge; and
    a housing having a first and second flexible tab members, a protrusion being formed on one surface of each tab, a holding member having a scent collecting pad member, said holding member having first and second sides, holes being formed in each side, the housing tab members being positioned within said holes, whereby a vacuum is created at said second end of said second means when pressurized gas is introduced to said second means from said gas cartridge which causes a scent to be drawn into the housing and collect on the collecting pad.

2. The device of claim 1 wherein said holding member is removably secured to said housing.

3. The device of claim 1 further including an extension member attached to one end of said pad member holder, said extension member having first and second tabs with protrusions formed on one surface of each tab, said extension member fitting over said scent pad holder and wherein said protrusions fit into the holes formed in said holding member, whereby said extension member is secured to said holding member.

4. The device of claim 3 further including an extension tube mounted on said extension member.

* * * * *